United States Patent [19]
Armstrong, Jr.

[11] Patent Number: 5,334,173
[45] Date of Patent: Aug. 2, 1994

[54] STABILIZING FOOT MEANS FOR CAP OF NEEDLE ASSEMBLY AND METHOD THEREOF

[75] Inventor: Michael Armstrong, Jr., Baltimore, Md.

[73] Assignee: Leonard Bloom, Towson, Md.; a part interest

[21] Appl. No.: 41,489

[22] Filed: Apr. 1, 1993

[51] Int. Cl.$^5$ ............................................. A61M 5/00
[52] U.S. Cl. .................................. 604/263; 604/192; 128/919
[58] Field of Search ............... 604/263, 192, 187, 198, 604/110, 414, 410–412; 128/919, 763; 206/365, 364, 367

[56] References Cited

U.S. PATENT DOCUMENTS

| | | |
|---|---|---|
| 3,107,785 | 10/1963 | Roehr . |
| 4,664,259 | 5/1987 | Landis . |
| 4,735,617 | 4/1988 | Nelson et al. .................. 604/192 |
| 4,742,910 | 5/1988 | Staebler . |
| 4,844,249 | 7/1989 | Coulombe . |
| 4,874,383 | 10/1989 | McNaughton . |
| 4,875,583 | 10/1989 | Nosanchuk . |
| 4,915,698 | 4/1990 | Levenson . |
| 4,921,199 | 5/1990 | Villaveces . |
| 4,973,315 | 11/1990 | Sincock . |
| 4,981,476 | 1/1991 | Aichlmayr et al. . |
| 5,007,535 | 4/1991 | Meseke et al. . |
| 5,038,929 | 8/1991 | Kubofcik . |
| 5,041,099 | 8/1991 | Gelabert . |
| 5,222,505 | 6/1993 | Burns ............................ 128/763 |

OTHER PUBLICATIONS

Jagger et al, "Rates of Needle-stick Injury Caused by Various Devices in a University Hospital", *New Englang Journal of Medicine*, 319 (5) 284–288 (1988).

Marcus et al, "Surveillance of Health Care Workers Exposed to Blood from Patients Infected with the Human Immunodefiency Virus", *New England Journal of Medicine*, 319 (17) 1118–1123 (1988).

Kaczmarek et al, "Multistate Investigation of Needle-handling by Health Care Workers", *MMJ*, 40 (11) 989–992 (1991).

*Primary Examiner*—C. Fred Rosenbaum
*Assistant Examiner*—V. Alexander
*Attorney, Agent, or Firm*—Leonard Bloom

[57] ABSTRACT

A protective cap (13') for a needle (12) has a stablizing foot (16), the bottom surface (17) of which is provided with an adhesive (18). When the needle (12) is removed from its sterile package (11), a protective cover (19) is peeled off the foot (16) to expose the adhesive (18). The foot (16) may then be adhered (temporarily) to a suitable supporting surface, such as a patient's roll-away table (14), so that the cap (13') is substantially in an upright or fixed position and will not fall over even if the table (14) is moved or jarred. After use on the patient, the used needle (12') is inserted within the cap (13') with a "snap" or other suitable interference fit and, thereafter, the assembled cap (13') and used needle (12') are simply lifted or otherwise removed from the table (14) and tossed into a suitable "sharps" container (23) for ultimate disposal. In a preferred embodiment (FIGS. 12A–12B) the protective layer (29) is automatically pulled away from the foot (16) as the needle and cap assembly (10) is removed from the sterile package (11).

1 Claim, 11 Drawing Sheets

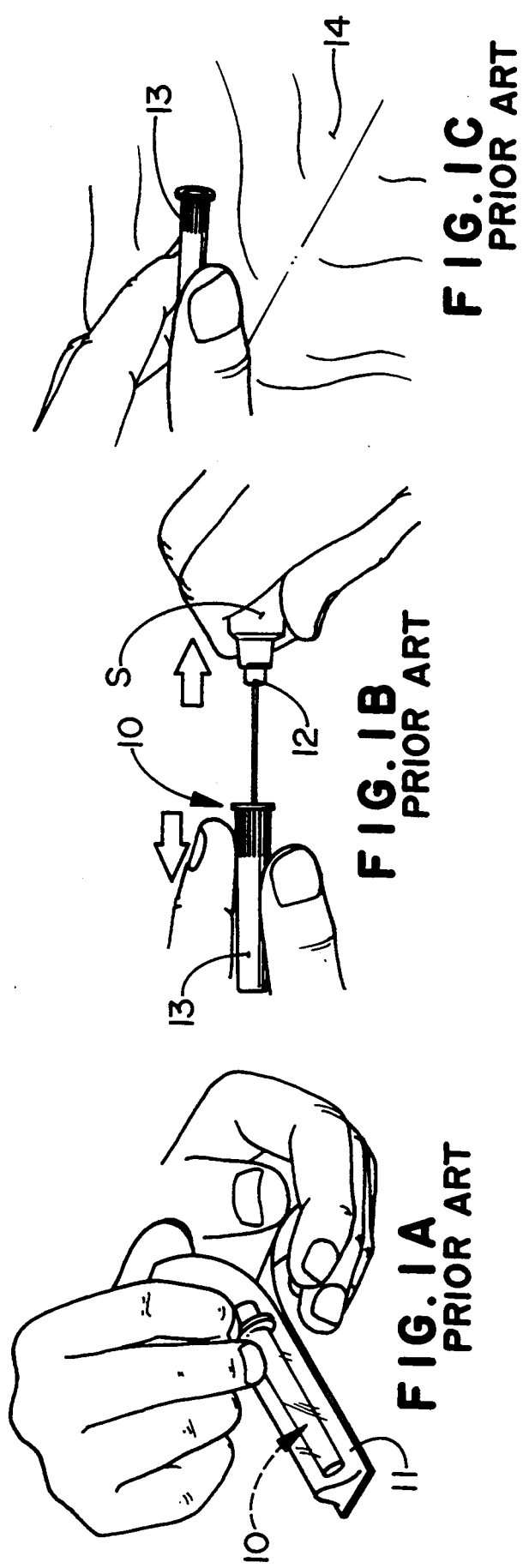
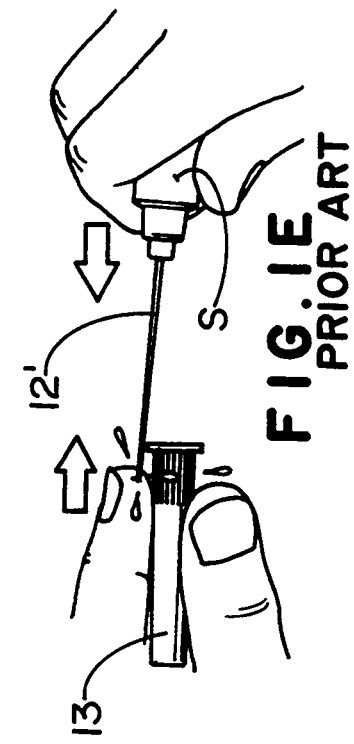

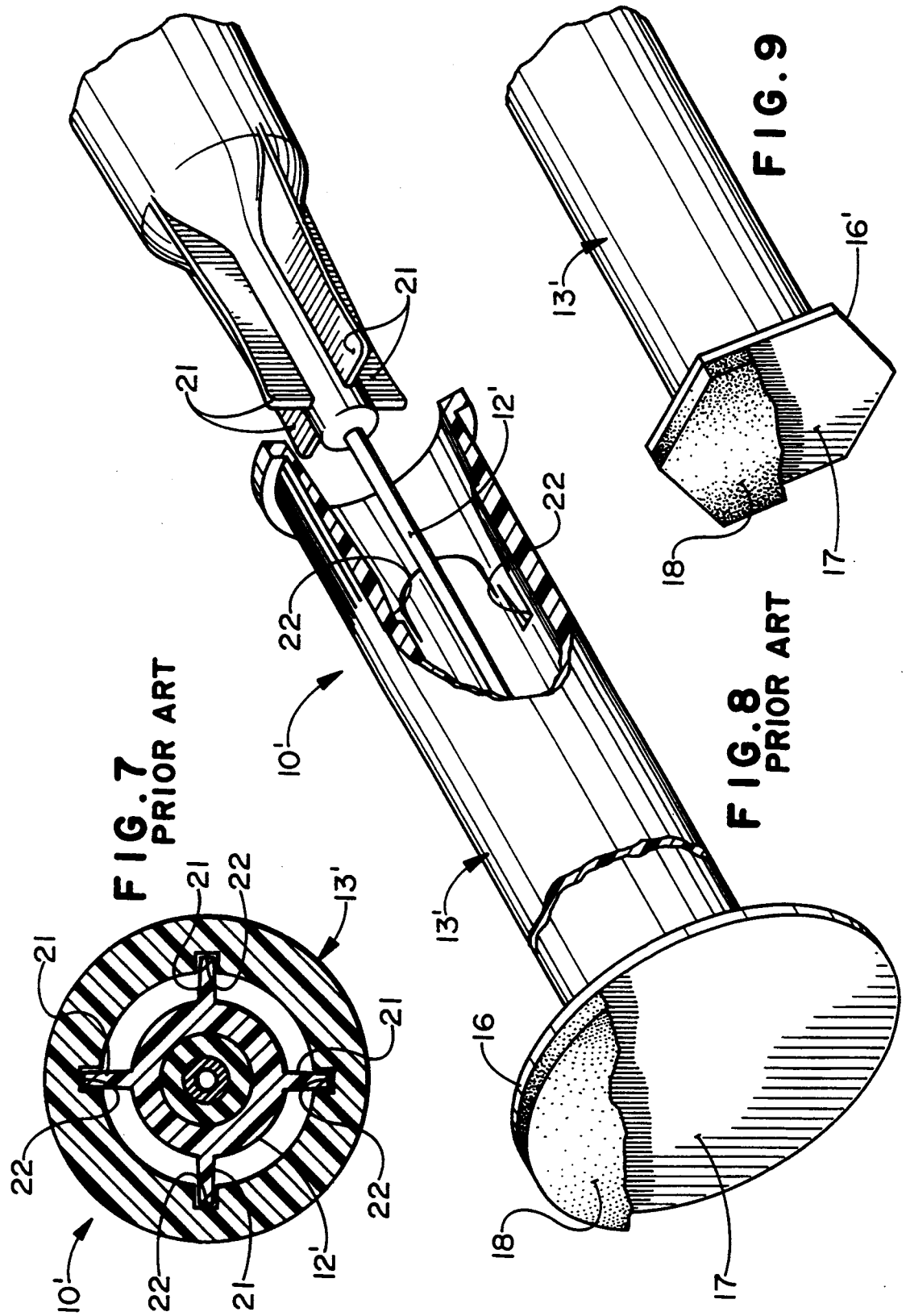

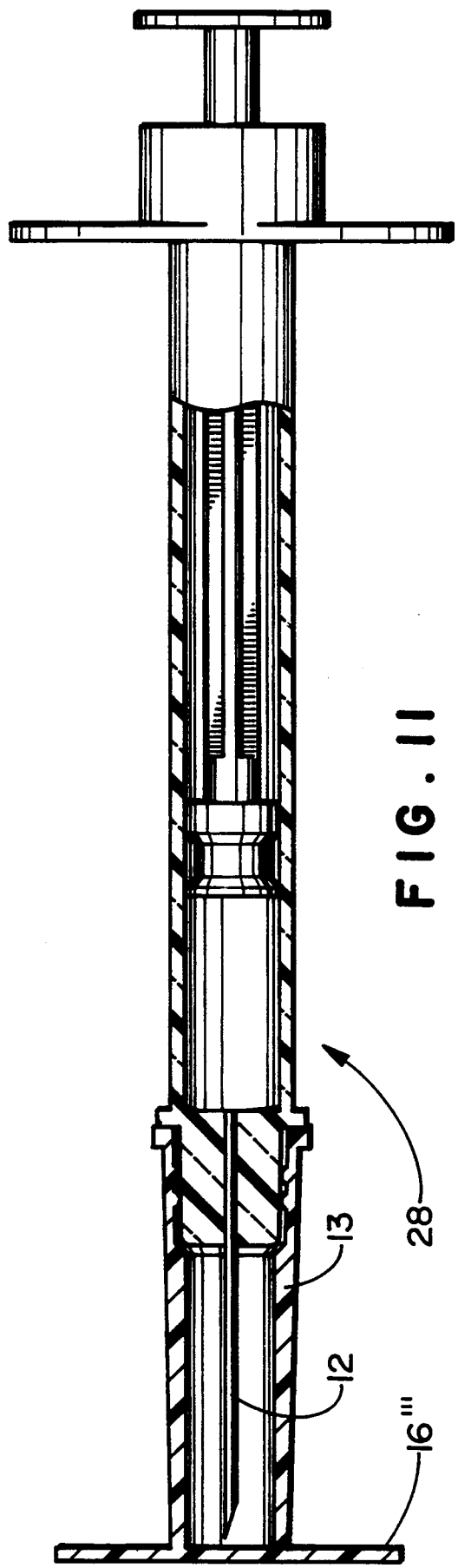

STABILIZING FOOT MEANS FOR CAP OF NEEDLE ASSEMBLY AND METHOD THEREOF

FIELD OF THE INVENTION

The present invention relates to a needle assembly used for medical purposes, and more particularly, to a needle assembly having a separable needle and cap.

BACKGROUND OF THE INVENTION

Millions of needles are used every day in hospitals, clinics and medical offices for taking blood samples, injecting fluids via a catheter, and for other purposes in the practice of clinical medicine. The needle is part of an overall assembly packaged in a suitable sterile container. The container is broken into, the needle assembly is removed, and the needle is withdrawn from its protective cover or cap. The needle is then used on a patient, as for example, in conjunction with a syringe.

Thereafter, the nurse (or other health care provider) often picks up the cap in one hand—and the used needle in the other hand—and inserts the used needle into the cap. Sometimes, and especially if the nurse is distracted or in a hurry, the nurse will miss the cap completely and accidentally stick her (or his) hand with the used needle. Some nurses even hold the cap between their lips, then insert the used needle into the cap; unfortunately, they sometimes miss and stick their lips or tongue!

Accordingly, there is a definite risk of acquiring the deadly human immunodeficiency virus (HIV) or "AIDS" virus from a patient. As reported by R. Marcus, "Surveillance Of Health Care Workers Exposed To Blood From Patients Infected With the Human Immunodeficiency Virus", New England Journal of Medicine, 1988, the risk of HIV transmission from a single needle-stick injury is approximately 0.4%. The risk of transmission of the hepatitis-B virus is even higher.

The results reported by Marcus are similar to a study conducted by the Needle Stick Surveillance Committee of the Centers For Disease Control ("CDC"). Their study showed that out of around 3,900 cases of needle sticks incurred by health care providers (where AIDS patients were involved) 13 health care providers—roughly 1 out of 300—subsequently tested HIV positive.

Even if routine testing of patients is performed, some HIV-infected individuals would test "false negative" since there is a six-month incubation period for the HIV virus. Because of the difficulty in determining which patients are infected with HIV, the CDC has issued guidelines called "Universal Precautions". Under these Universal Precautions, all patients are treated as if infected with the AIDS virus; and all bodily fluids which may be contaminated with blood, semen or other internal body fluids are assumed to be infectious.

The greatest risk of transmission occurs from parenteral exposure (i.e., through broken skin) to contaminated instruments. Eighty percent (80%) of exposures reported by Marcus were due to needle-sticks and eight percent (8%) were due to cuts with HIV contaminated instruments. Thirty-five percent (35%) of needle stick injuries involve disposable syringes, and twenty-five percent (25%) involve intravenous tubing and needle assemblies (as reported by Jagger et al "Rates Of Needle-Stick Injury Caused By Various Devices In A University Hospital, New England Journal of Medicine, 1988). Furthermore, seventeen to thirty percent (17–30%) of these needle stick injuries occur while recapping used needles (from Marcus, Jagger).

As a result, the CDC has recommended that recapping of needles be abandoned, and that needles be promptly discarded into a puncture-resistant "sharps" container. Despite widespread promulgation of these recommendations by the CDC, health care workers continue to recap 21.5% of used needles (as reported by Kaczmarek et al, "Multistate Investigation Of Needle-Handling by Health Care Workers", MMJ, 1991).

If a health care worker is exposed to the blood of a known AIDS patient, periodic testing is required (more or less indefinitely) to determine if the worker has become HIV positive. This is an inconvenient, worrisome, costly and time-consuming procedure. Besides, the very threat of becoming HIV positive from a needle stick injury is disconcerting and distracting and interferes with the worker's concentration on the job. Additionally, the health care worker may refrain from intimate relations and may delay childbearing to protect his or her partner and children from possibly acquiring the deadly AIDS virus.

Moreover, the failure to properly dispose of "sharps" has led to countless injuries among housekeeping, laundry and janitorial personnel.

The problem of safely recapping a used needle has long been recognized in the prior art. For example, U.S. Pat. No. 5,041,099 issued to Gelabert on Aug. 20, 1991, discloses a non-reusable syringe in which the cap has three splayed feet on the end thereof, and the cap is intended to remain in an upright position while recapping the needle. However, if the cap is placed on an uneven surface or on a patient's roll-away table (which is on casters) the cap will be unsteady, and the cap will fall over if the table is jarred.

Additionally, some disposable instrument trays provide a channel for placement of the needle cap. Nevertheless, the acceptance of these prior art devices has been quite limited.

Needle stick injuries remain an occupational hazard, and the risk continues to escalate as the AIDS disease multiplies. As a result, doctors, nurses and other health care workers have modified their practices or, in some cases, have quit their jobs altogether.

SUMMARY OF THE INVENTION

Accordingly, it is an object of the present invention to alleviate the risk associated with the disposal of used needles by providing a safe and convenient means for replacing the cap on a used needle.

It is another object of the present invention to provide a stabilizing foot on the cap, so that the cap may be conveniently supported on a suitable surface, thereby facilitating a one-hand insertion of the used needle into the cap.

The present invention is applicable to a needle assembly for medical purposes; wherein the needle assembly includes a needle and further includes a separable cap having an end portion; and wherein, after use on a patient, the used needle is intended to be received within the cap with a "snap" (or other suitable fit) for subsequent disposal of the used needle and its cap.

In accordance with the teachings of the present invention, a stabilizing foot is provided on the end portion of the cap. The foot has a bottom surface provided with an adhesive, and a protective cover is provided for the adhesive. As a result, the cover may be removed to expose the adhesive, thereby enabling the cap to be mounted temporarily on a supporting surface, such as on a patient's table. After use on the patient, the used needle may be conveniently inserted within the cap—in a one-hand operation—and, thereafter, the assembly of the used needle and cap may be removed from the supporting surface for ultimate disposal.

The stabilizing foot on the cap may be in the form of a round disk and, in a preferred embodiment, is polygonal to prevent the cap from rolling if placed horizontally on a patient's table.

In accordance with another embodiment of the present invention, the protective cover is automatically peeled away (from the adhesive on the bottom of the stabilizing foot) as the cap is removed from its sterile package.

Viewed in another aspect, the present invention comprises an improved method of disposing of a used needle in a medical environment. This improved method includes the steps of: providing a sterile needle package, opening the package and removing the needle, removing a cap from the needle, and temporarily fastening the cap on a suitable supporting surface, such that the cap is substantially perpendicular to the supporting surface, and such that the cap will not fall over in the event the supporting surface is accidentally hit or jarred. After the needle is used on a patient, the used needle is slipped into the cap—using only one hand—such that the cap is attached to the used needle; and thereafter the used needle and cap attached thereto are removed from the supporting surface for ultimate disposal.

Thus, the nurse or other health care worker is not required to hold or support the cap or cover in any way, thereby virtually eliminating the possibility of a needle stick during the recapping process.

These and other objects of the present invention will become apparent from a reading of the following specification taken in conjunction with the enclosed drawings.

BRIEF DESCRIPTION OF THE DRAWINGS

FIGS. 1A–1E show, pictorially, the problems inherent in the prior art disposal of used needles.

FIG. 1A shows the assembly of the needle and cap being removed from its sterile package.

FIG. 1B shows the needle being removed from its cap.

FIG. 1C shows the cap being laid down on a suitable surface, such as on a patient's table.

FIG. 1D shows the needle being used on a patient, as for example, drawing blood from the patient.

FIG. 1E shows the risk involved in replacing the cap on the needle, occasionally resulting in a needle stick.

FIG. 2A shows the improved needle assembly of the present invention being removed from its sterile package.

FIG. 2B shows the protective cover being peeled away from a stabilizing foot on the end of the cap, thereby exposing an adhesive on the bottom of the foot.

FIG. 2C shows the needle being removed from the improved cap of the present invention.

FIG. 2D shows the foot being stuck on a patient's table, such that the cap is upright, steady, and in a prominent position.

FIG. 2E corresponds to a portion of FIG. 2D, drawn to an enlarged scale.

FIG. 2F shows the needle being used on a patient, corresponding to FIG. 1D.

FIG. 2G corresponds substantially to FIG. 2E, but shows the used needle being inserted into the cap in a one-hand movement.

FIG. 2H shows the assembly of the used needle and cap being lifted off or otherwise removed from the patient's table (or other supporting surface) without marring the finish of the patient's table.

FIG. 2I shows how the cap may be temporarily secured on a wall and held in a horizontal position, if desired.

FIG. 2J shows how the assembly of the cap and used needle may be withdrawn from the wall by a simple rocking movement to exert a torque on the assembly.

FIG. 2K shows the subassembly of the used needle and cap being tossed into a "sharps" container.

FIG. 7 is a cross-sectional view thereof, taken across the lines 7—7 of FIG. 6, and drawn to an enlarged scale.

FIG. 8 is an exploded perspective view of the needle and cap, showing the stabilizing foot of the invention, and further showing a conventional prior art means for engaging the needle and cap with a snap or other suitable interference fit.

FIG. 9 corresponds to a portion of FIG. 8, but shows an alternate embodiment in which the stabilizing foot is polygonal.

FIG. 11 is a longitudinal cross-sectional view, with certain parts shown in elevation, of an integral syringe and needle having the stabilizing foot of the present invention.

GENERAL DESCRIPTION OF THE PREFERRED EMBODIMENT

Figure 2C:
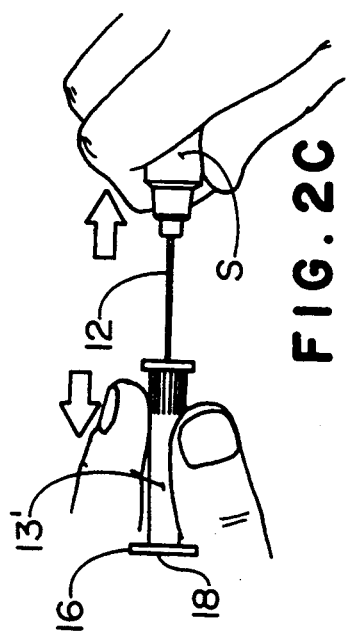
FIG. 2A–2K show, pictorially, the improvement of the present invention, wherein the risk of a needle stick has been substantially reduced if not eliminated altogether.
Figure 2F:
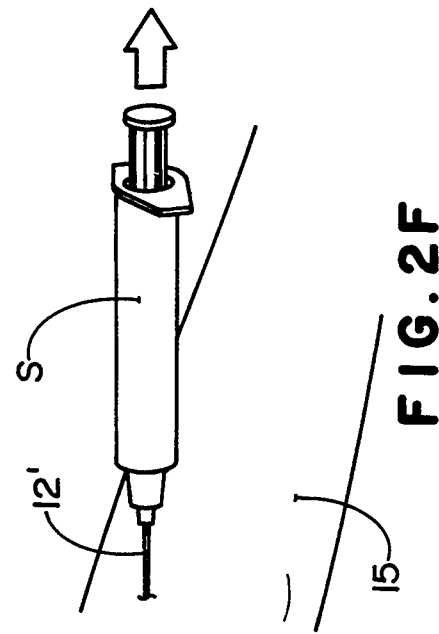
Figure 2B:
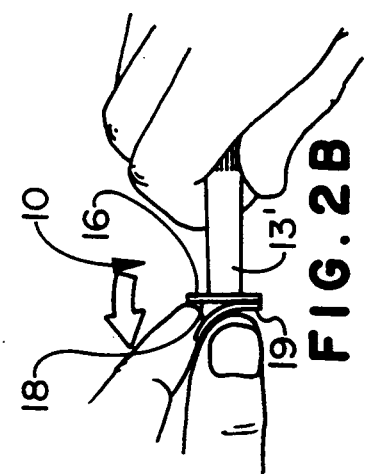

With reference to FIGS. 1A–1E, which pictorially illustrate the problems inherent in the prior art, a conventional needle assembly 10 is removed from its sterile package 11 (FIG. 1A) and, thereafter, the needle 12 is removed from its protective cap 13 (FIG. 1B). The needle 12, such as those supplied by Becton Dickinson & Co. of Franklin Lakes, New Jersey under its trademark "PrecisionGlide", is widely used in hospitals and clinics; it is only one example of needles to which the teachings of the present invention may find particular utility.

The cap 13 is merely laid down on a suitable surface such as the patient's table 14 (FIG. 1C). The nurse (or other health care provider) inserts the needle 12 into a patient's arm 15 (FIG. 1D) as, for example, with a conventional syringe S. When the nurse finishes with the patient, the used needle 12' is often inserted back into its cap 13.

As shown more clearly in FIG. 1E, this requires the nurse to grasp the used needle 12' with one hand and to grasp the cap 13 with the other hand and to insert the used needle 12' into the cap 13, as the nurse's hands move toward each other. Unfortunately, however, the nurse may miss the cap 13 and become stuck with the used needle 12'. Accordingly, there is a definite risk of acquiring an infectious disease which, in severe cases, can lead to the nurse's death.

Figure 2E:
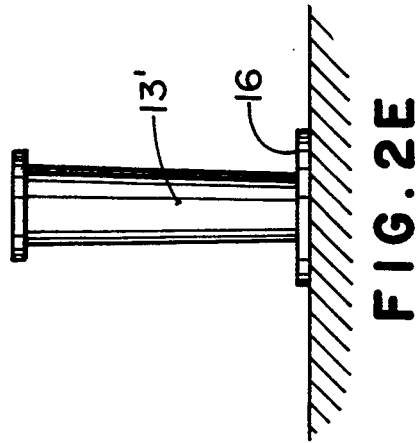
Figure 2A:
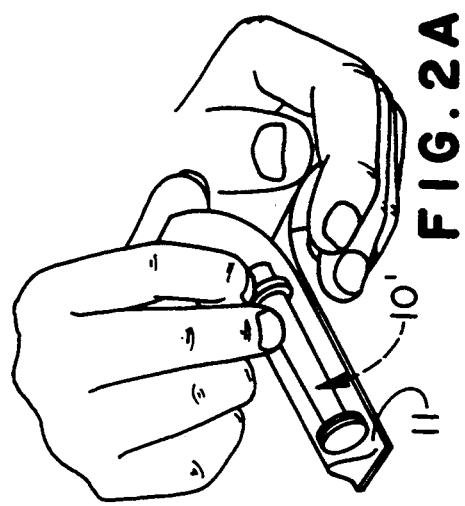
Figure 2D:
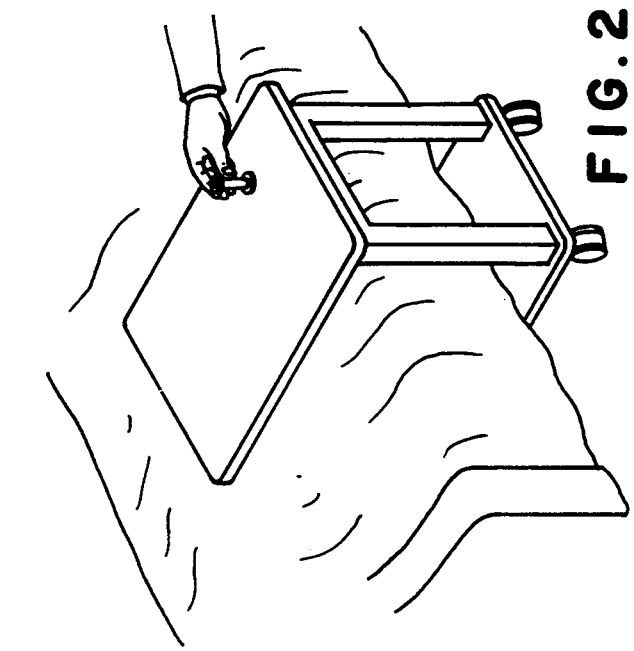
Figure 2G:
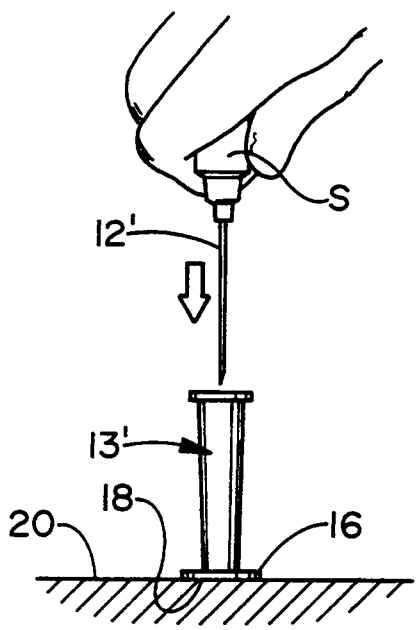
Figure 2H:
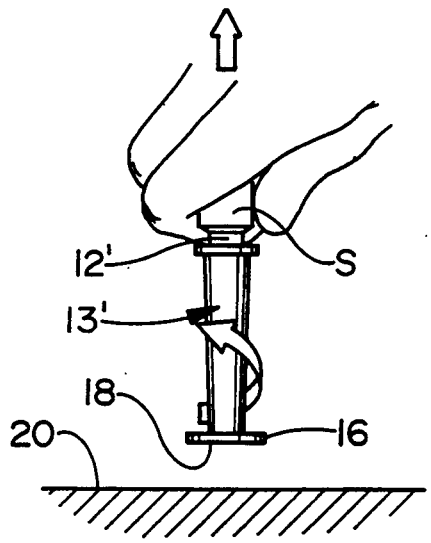
Figure 2I:
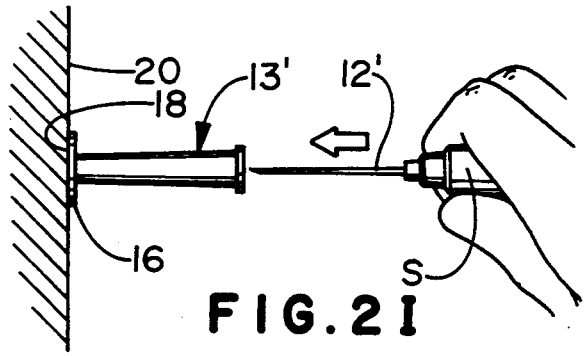
Figure 3:
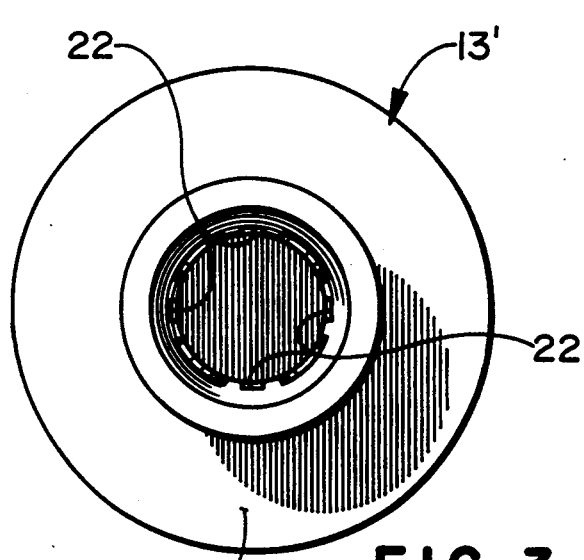
FIG. 3 is a top plan view of the improved cap, showing the stabilizing foot on the end of the cap.
Figure 4:
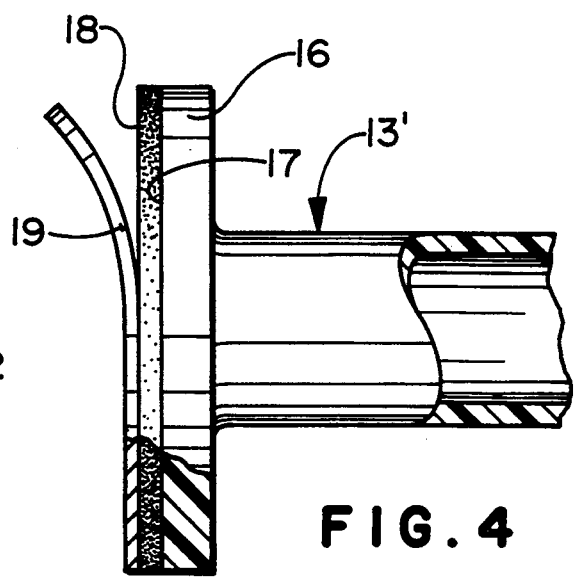
FIG. 4 is a side elevational view thereof, partly in section and partly in elevation, and showing the stabilizing foot, adhesive and protective cover therefor.
Figure 5:
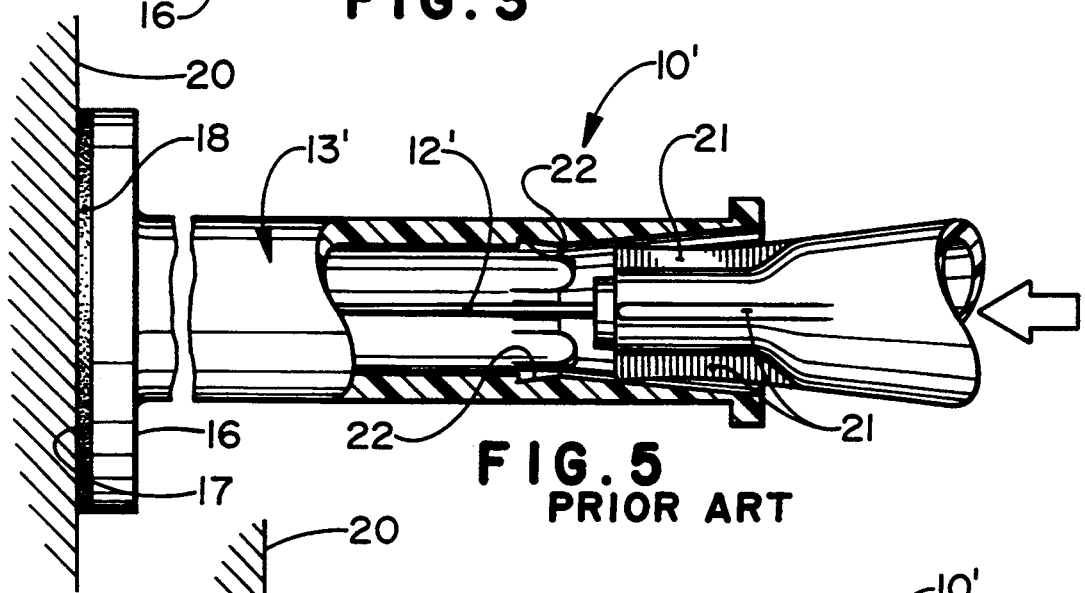
FIG. 5 shows the used needle being inserted into the improved cap, certain parts being broken away and sectioned, and showing the manner in which the used needle is received in the cap with a "snap" or other suitable interference fit.
Figure 6:
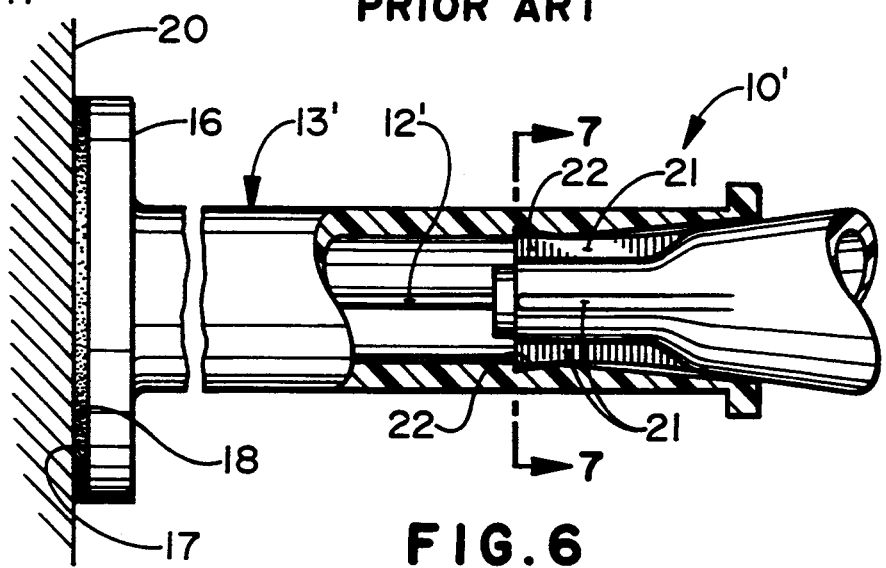
FIG. 6 corresponds substantially to FIG. 5, but shows the used needle snapped into the cap for convenient disposal.

With reference to FIGS. 2A–2I, and with further reference to FIGS. 3–8, the improved needle assembly 10' of the present invention has a stabilizing foot 16 on its cap 13'. Preferably, the stabilizing foot 16 is integrally molded on the cap 13' and, in one embodiment, comprises a round relatively-thin disk (FIGS. 3 and 8). The foot 16 has a bottom surface 17 provided with a suitable adhesive 18 or other sticky surface. Preferably, the adhesive 18 is protected by a cover 19, and the cover 19 may be easily peeled off (FIGS. 2B and 4) to expose the adhesive 18. The cap 13', and more particularly its foot 16, may then be stuck (temporarily) on a suitable supporting surface, such as on a patient's rollaway table 14 (FIGS. 2D and 2E).

Figure 2J:
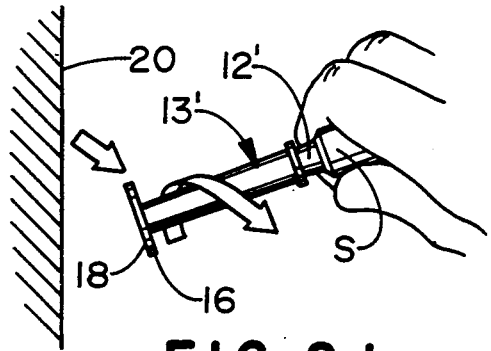

If desired, the cap 13' may be stuck (horizontally) on a side wall 20 adjacent to the patient (FIGS. 2I and 2J). This is simply not possible with the protective caps or covers heretofore disclosed in the prior art.

In each case, the self-adhering cap 13' is in a steady substantially-upright position, substantially perpendicular to its supporting surface 14 (or 20) and prominently displayed so that the cap 13' will not become inadvertently misplaced, nor tip over during replacement of the used needle 12'.

When the used needle 12' is to be discarded, the nurse merely slips the used needle 12' into the cap 13' in a one-handed operation or movement as shown more clearly in FIG. 2G. Since the cap 13' is temporarily glued on to the patient's table 14 (or supporting surface 20), the cap 13' is in a substantially constant position without easily falling over or wobbling, even if the patient's table 14 is accidentally hit or jarred.

Figure 2K:
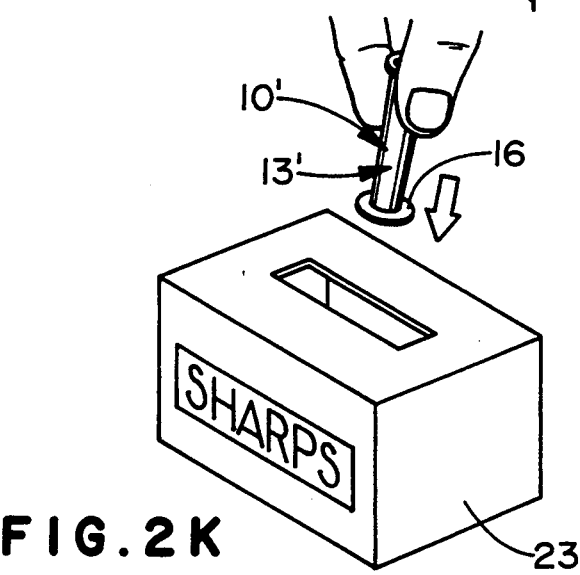

Thereafter, the assembly of the used needle 12' and its cap 13' is simply removed from its supporting surface and safely disposed of in a conventional "sharps" container 23 (FIG. 2K). The assembly of the used needle 12' and its cap 13' may be lifted off the patient's table 14 (FIG. 2H) or twisted off the side wall 20 (FIG. 2J).

Any suitable means may be employed to retain the used needle 12' within the cap 13'. One embodiment, well known in the prior art, is shown in FIGS. 5–8. There, the used needle 12' has a plurality of circumferentially-spaced protruding ribs 21 engaging a cooperating plurality of circumferentially-spaced ramps 22 formed internally within the cap 13', so that the used needle 12' is received within the cap 13' with a slight interference fit. As will be appreciated by those skilled in the art, however, other means of removably retaining the used needle 12' and cap 13' may be employed, if desired.

In one embodiment, the force required to remove the assembly of the used needle 12' and cap 13' off of the patient's table 14 (or other supporting surface 20) is less than the force required to remove the used needle 12' from the cap 13'. Thus, the retention force of the adhesive 18 is sufficient to temporarily retain the cap 13' in its upright steady position, but insufficient to allow the used needle 12' to again pull out of its protective cap 13' when the assembly of the used needle 12' and cap 13' is removed from the patient's table 14 (or other supporting surface 20). This assures that the used needle 12' and cap 13' will remain in an assembled condition when removed from the patient's table 14 (or other supporting surface 20) and disposed of in the "sharps" container 23. The disposal is fast and easy and substantially reduces, if not eliminates entirely, the danger of a needle stick and the pain and risk, as well as the discomfort and costs associated with periodic testing and monitoring.

With reference to FIG. 9, the foot 16' is hexagonal (or other polygonal configuration) to prevent rolling if the cap 13' is placed on its side.

It will be appreciated that the present invention facilitates recapping of a used needle in a manner in which the nurse's hand is "behind" the used needle 12', and in which the nurse's hand is not moved in a direction towards the used needle 12'. The stabilizing foot 16 with its adhesive surface 18 is built-in integrally with the cap 13; it is not a separate accessory. Thus, a safety feature is provided which is readily available, and recapping and disposal of the used needle is simple and quick and requires minimal training. Moreover, the safety feature of the present invention is not unwieldy or cumbersome and may be manufactured economically in high volume without significant changes in the existing production processes.

The present invention is applicable to a wide variety of needles and related devices used for medical and clinical purposes. Another example, as shown in FIGS. 10A–10G, is an intravascular over-the-needle catheter 24, such as those supplied by Baxter Healthcare Corporation of Deerfield, Illinois under its registered trademark "QUICK-CATH". This catheter 24 includes a needle 25, a catheter connection 26, and a cap 13".

Figure 10A:
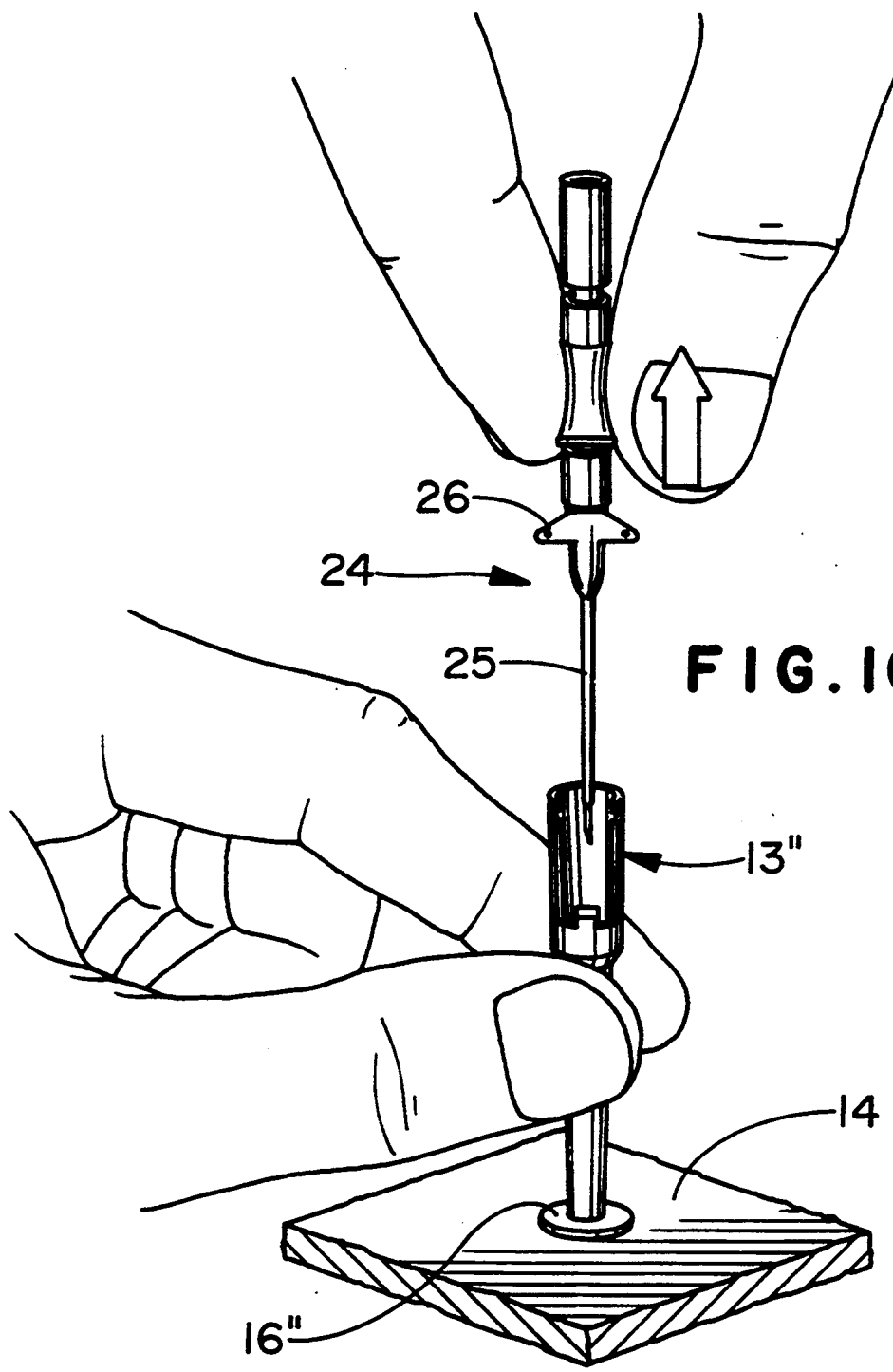
FIGS. 10A–10G are pictorial sequence views, corresponding substantially to those of FIGS. 2A–2K, but showing the application of the present invention to an intravascular over-the-needle catheter.
Figure 10B:
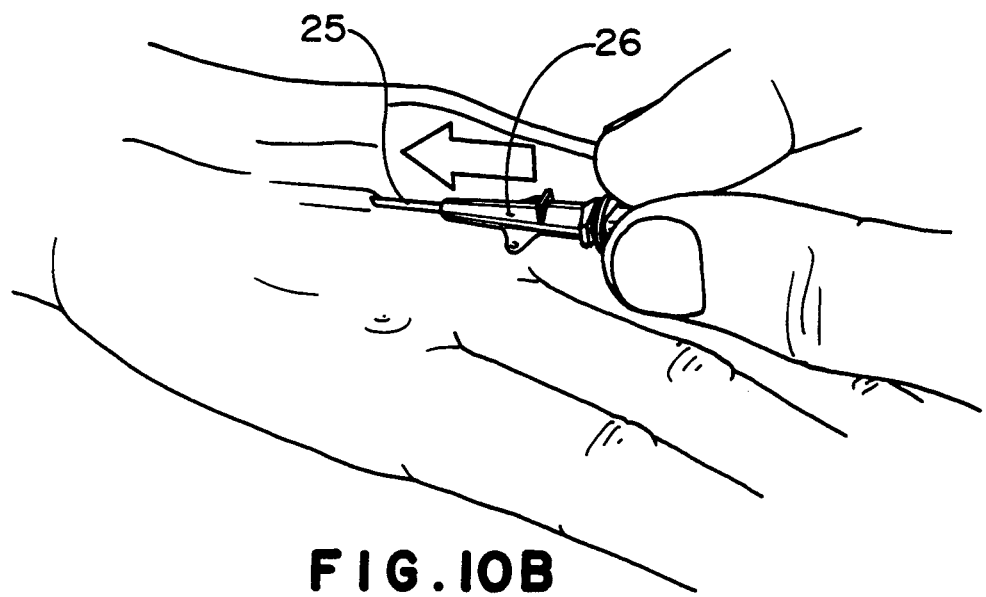
Figure 10C:
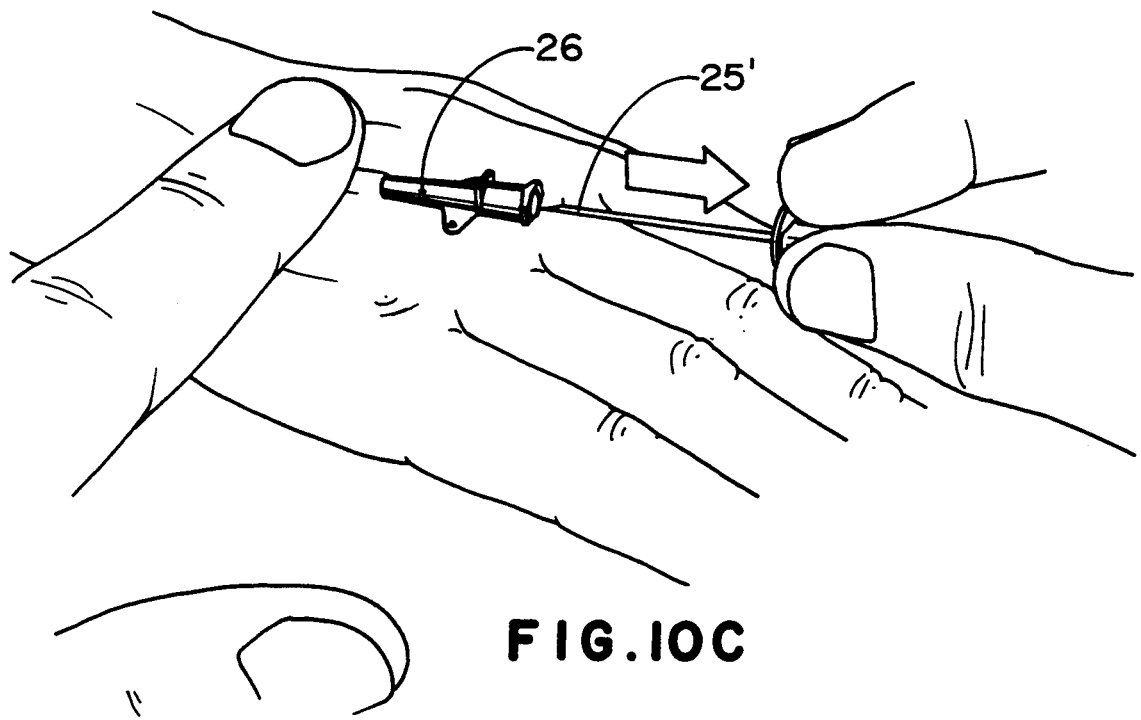
Figure 10D:
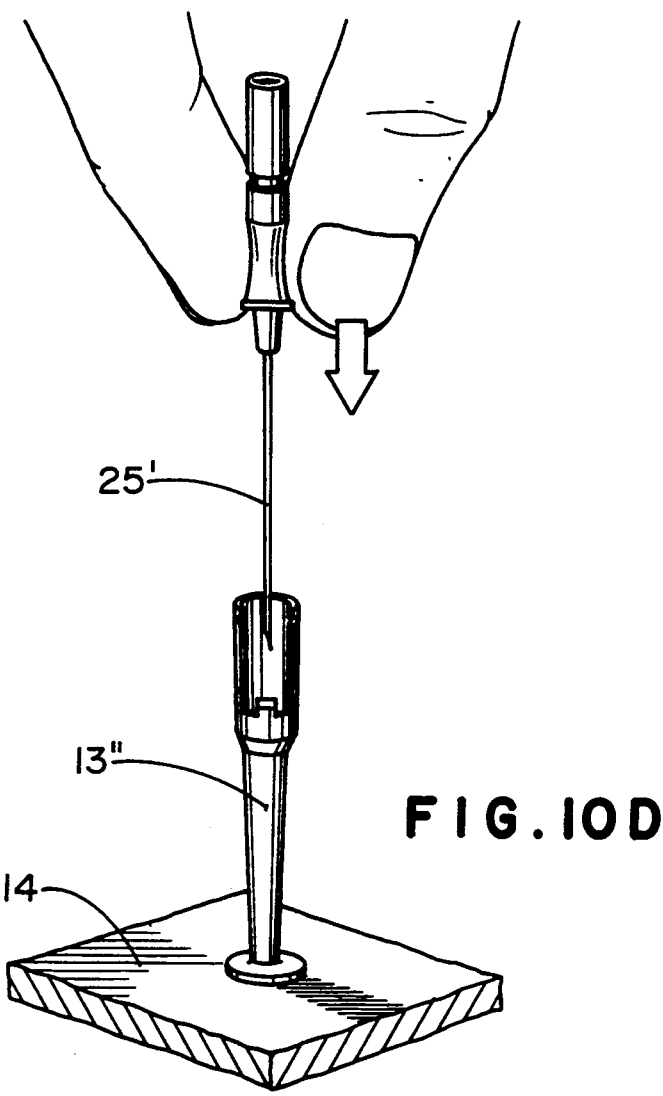

In accordance with the teachings of the present invention the cap 13" is provided with a stabilizing foot 16', the bottom surface of which has a suitable adhesive or its equivalent (not shown). The cap 13" may be placed on a supporting surface such as the patient's table 14 (FIG. 10A) and the needle 25 and catheter connector 26 are removed from the cap 13" (FIG. 10B). The needle 25 is inserted into a patient's vein (FIG. 10C) and, thereafter, the used needle 25' is withdrawn and reinserted into the cap 13" (FIG. 10D) in a one-hand movement.

Figure 10E:
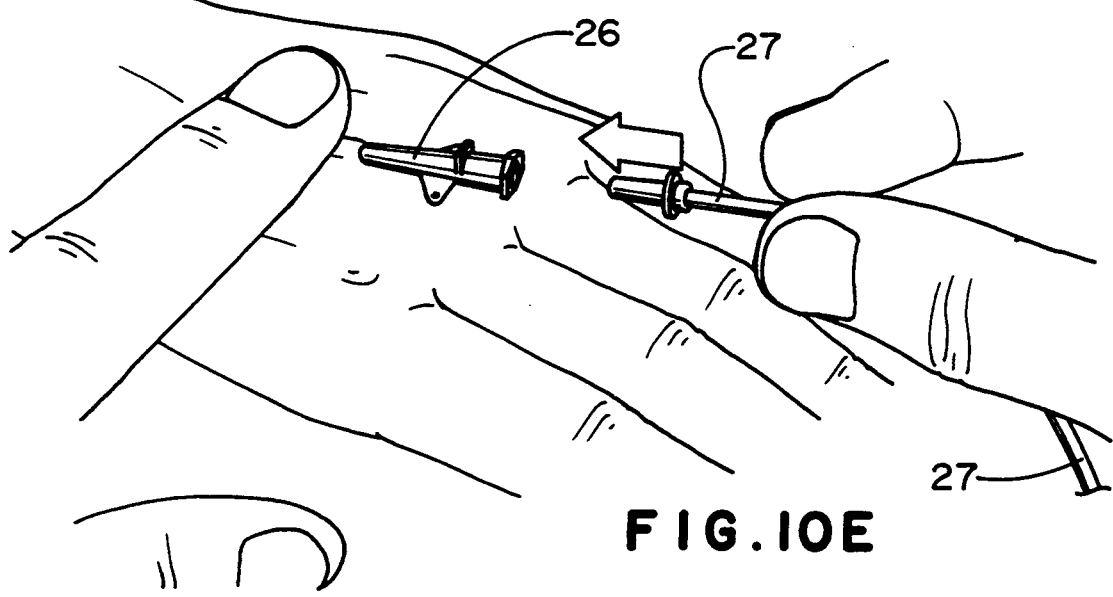
Figure 10F:
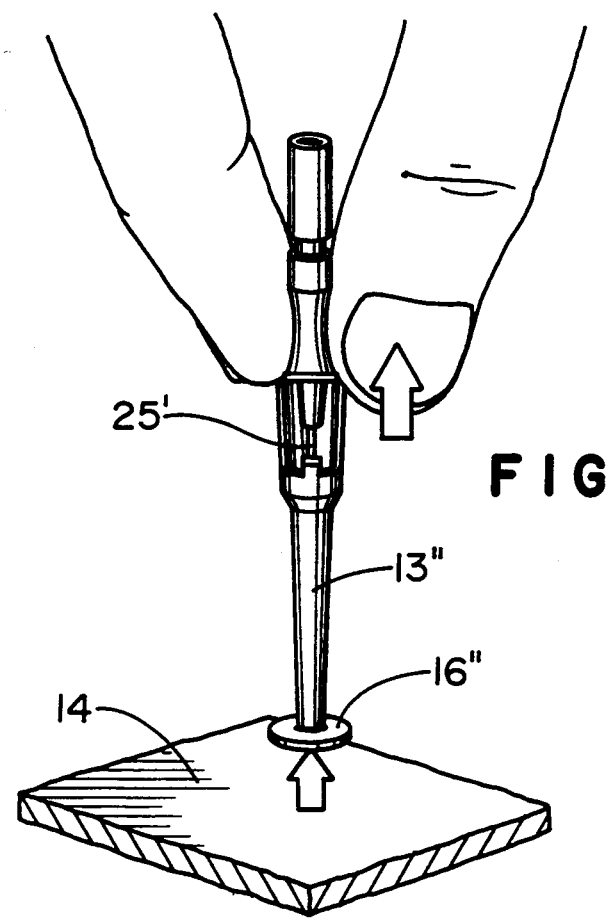
Figure 10G:
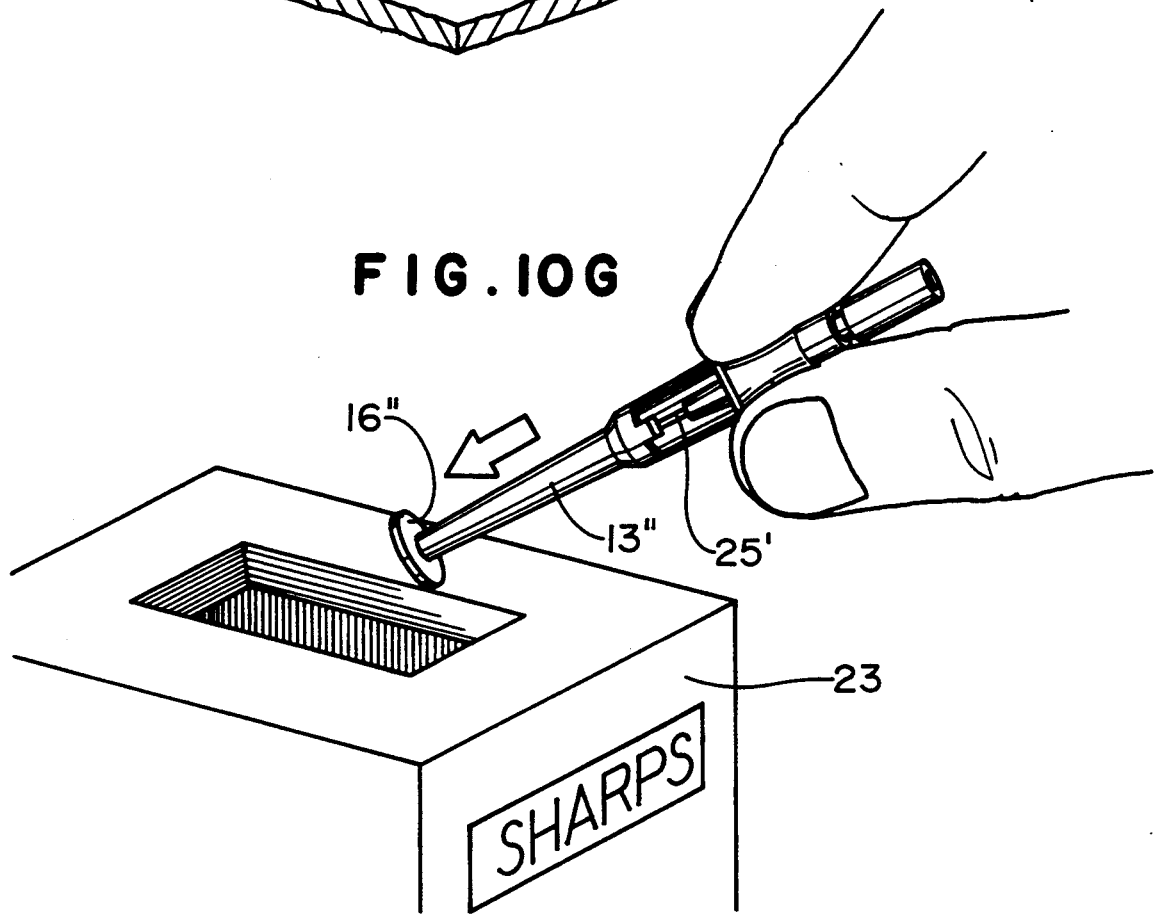

It is precisely when the used needle 25' is withdrawn that the risk of a needle stick is perhaps the greatest. It is essential that the nurse quickly connect the I.V. tube 27 (FIG. 10E) while holding down the patient's vein and preventing blood flow therefrom. At the same time, the nurse must dispose of the used needle 25'. This procedure becomes a "three handed" task. Usually, the nurse will merely set the used needle 25' on the bed or table for later retrieval or else hold it on her body in some fashion. With the advantage of the present invention, however, the nurse may replace the used needle 25' into the upright cap 13" (FIG. 10D) in a quick and convenient one-hand movement so that the catheter 26 may be quickly connected to the I.V. tube (FIG. 10E).

Thereafter, the assembly of the used needle 25' and its protective cap 13'' may be removed from the patient's table 14 (FIG. 10F) and discarded in the "sharps" container 23 (FIG. 10G) for safe removal and disposal.

With reference to FIG. 11, an integral needle and syringe assembly 28 is provided with a stabilizing foot 16'''. The operation of this embodiment of the invention, and its features and advantages, are substantially identical to those of the previous embodiments herein described. One example of the integral needle and syringe assembly 28 is the ½cc U-100 Insulin Syringe supplied by Becton Dickinson & Co. of Franklin Lakes, New Jersey under its registered trademark "MICROFINE".

Figure 12A:
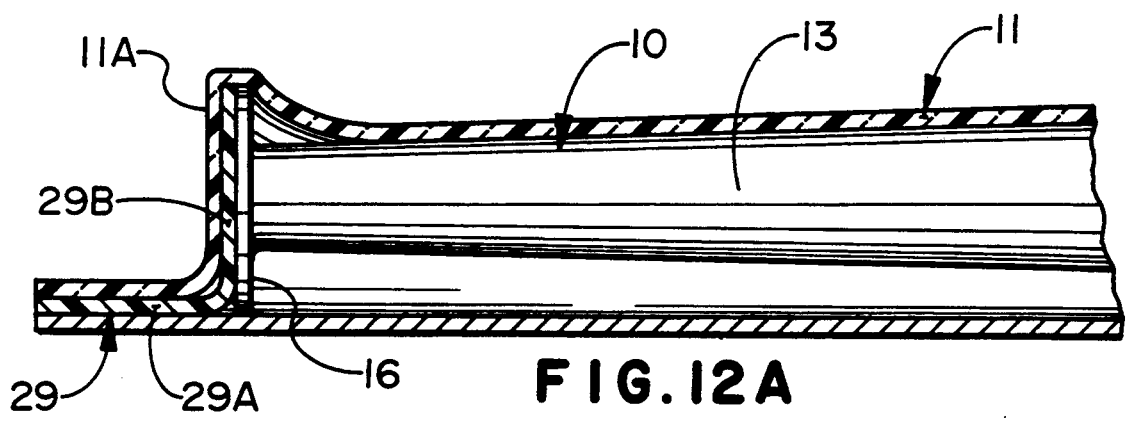
FIGS. 12A–12C are pictorial sequence views of a further embodiment, wherein the protective cover (for the adhesive on the bottom of the stabilizing foot) is automatically peeled off as the cap is removed from the sterile needle package.
Figure 12B:
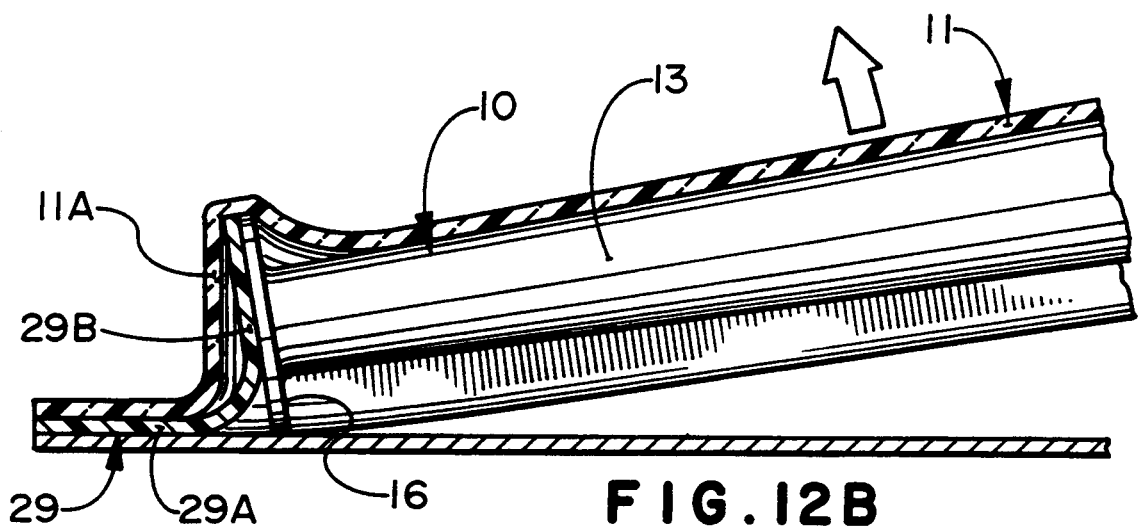
Figure 12C:
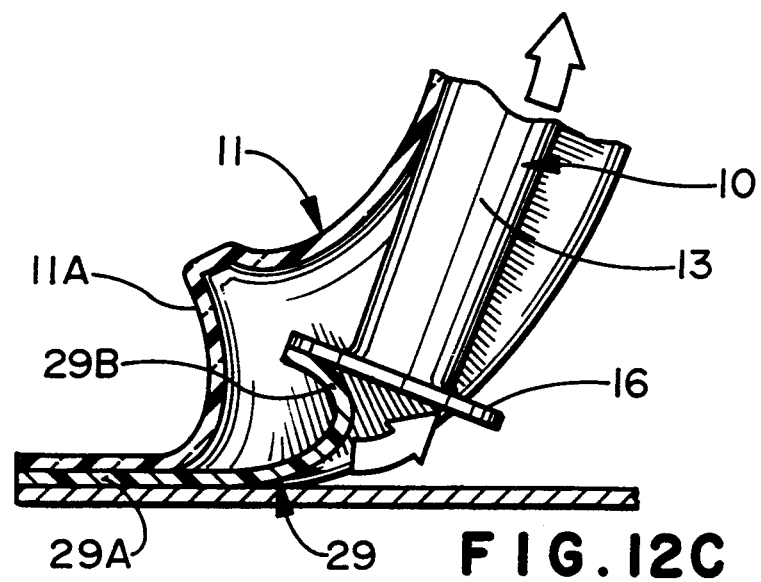

With reference to FIGS. 12A–12C, the sterile needle package 11 is provided with an inner layer 29 (FIG. 12A) serving as the protective cover for the adhesive on the bottom of the stabilizing foot 16 on the cap 13. This inner layer 29 has a first portion 29A which is anchored in the sterile package 11 and further has a second portion 29B disposed (or sandwiched) between the foot 16 and a wall 11A on the sterile package 11, as clearly shown in FIGS. 12A–12C. As the cap 13 is removed from the package 11 (FIG. 12B) the protective layer 29 is automatically peeled away or otherwise stripped off of the foot 16 (FIG. 12C). This embodiment eliminates the step of manually removing the protective cover 19 from the adhesive 18.

Obviously, many modifications may be made without departing from the basic spirit of the present invention. Rather, the teachings of the present invention are equally applicable to a wide variety of needle and cap designs. Accordingly, it will be appreciated by those skilled in the art that within the scope of the appended claims, the invention may be practiced other than has been specifically described herein.

I claim:

1. In a needle and cap assembly for medical use, wherein the assembly is contained in a sterile package, the sterile package having at least one wall, wherein the assembly includes a needle and further includes a cap having a foot, the foot having a bottom surface provided with an adhesive, and a peel-off protective cover for the adhesive, and wherein upon removal from the sterile package, the cap is stuck onto a supporting surface, such that the needle, after use, may be reinserted into the cap in a one-hand operation, thereby avoiding a needle stick, the improvement wherein, in the sterile package, the protective cover for the adhesive has a first portion anchored to the sterile package and further has a second portion disposed between the wall of the sterile package and the foot on the cap, such that as the sterile package is broken open and the assembly is pulled out of the sterile package, the first portion of the protective cover remains with the sterile package while the second portion of the cover is separated from the foot, thereby automatically exposing the adhesive on the foot.

* * * * *